(12) United States Patent
Li

(10) Patent No.: US 8,186,879 B2
(45) Date of Patent: May 29, 2012

(54) PANEL SUPPORT DEVICE AND X-RAY APPARATUS

(75) Inventor: Yuqing Li, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 206 days.

(21) Appl. No.: 12/724,743

(22) Filed: Mar. 16, 2010

(65) Prior Publication Data
US 2010/0232576 A1    Sep. 16, 2010

(30) Foreign Application Priority Data

Mar. 16, 2009    (CN) .......................... 2009 1 0128671

(51) Int. Cl.
*H01J 31/49* (2006.01)
(52) U.S. Cl. ...................................................... 378/189
(58) Field of Classification Search .................. 378/189, 378/190, 177, 181
See application file for complete search history.

(56) References Cited

U.S. PATENT DOCUMENTS

| 3,504,180 | A | | 3/1970 | Tone |
| 4,303,327 | A | | 12/1981 | LaBelle et al. |
| 4,365,344 | A | * | 12/1982 | Dornheim .................... 378/189 |
| 4,947,419 | A | | 8/1990 | Schmidt et al. |
| 5,652,781 | A | | 7/1997 | Armbruster et al. |
| 5,912,944 | A | | 6/1999 | Budinski et al. |
| 7,604,403 | B2 | | 10/2009 | Yi |
| 2005/0175155 | A1 | | 8/2005 | Wendlandt et al. |

FOREIGN PATENT DOCUMENTS

| JP | 11-155850 | 6/1999 |
| JP | 11-188022 | 7/1999 |

* cited by examiner

*Primary Examiner* — Irakli Kiknadze
(74) *Attorney, Agent, or Firm* — Armstrong Teasdale LLP

(57) ABSTRACT

A panel support device for detachably supporting an X-ray receiving panel includes a support plate configured to be in contact with the surface of the panel opposite to an X-ray receiving surface of the panel while the panel is mounted, a locking member for locking the panel on the support plate while the panel is mounted, and a drive device for driving the locking member so that the locking member is withdrawn from a locking position when the panel approaches the support plate and the locking member returns to the locking position when the panel comes in contact with the support plate in a process for mounting the panel.

18 Claims, 13 Drawing Sheets

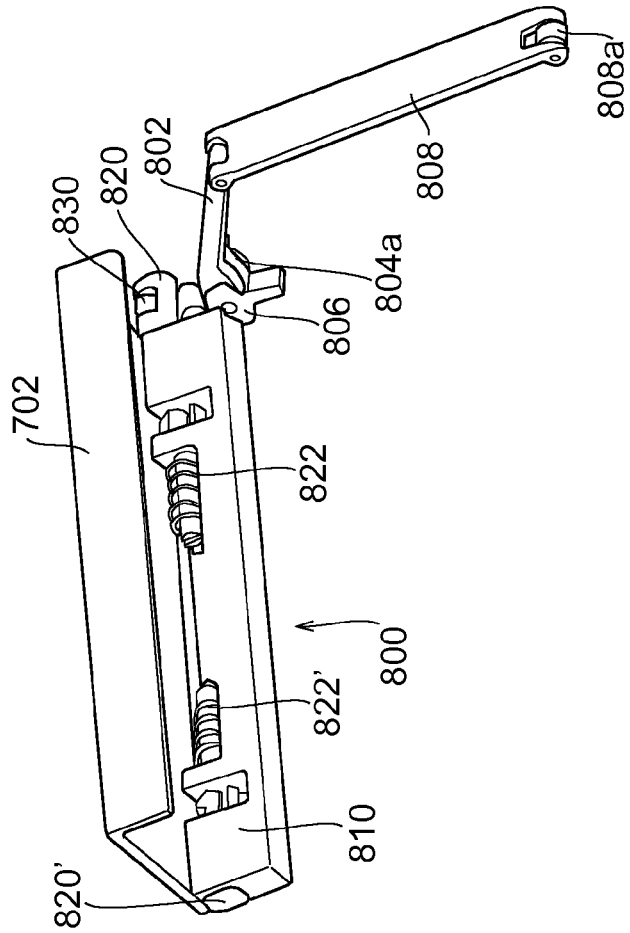
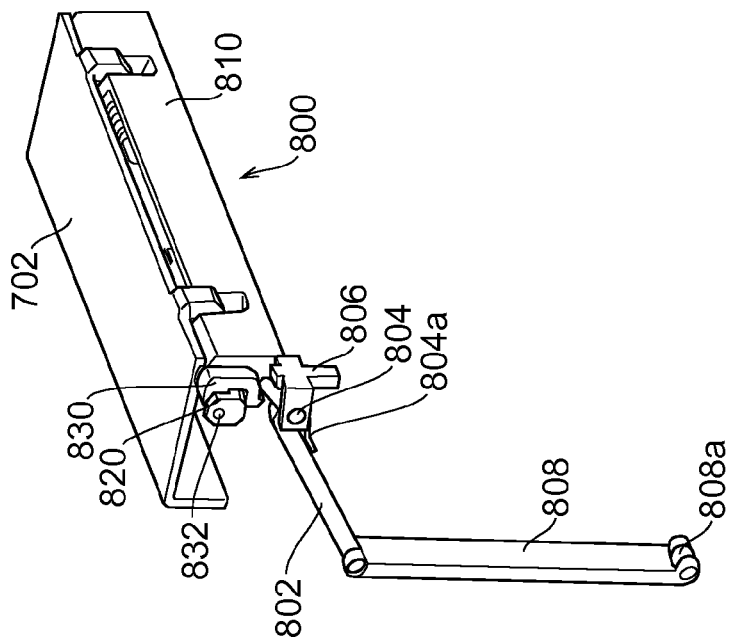
FIG. 6B
FIG. 6A

PANEL SUPPORT DEVICE AND X-RAY APPARATUS

CROSS REFERENCE TO RELATED APPLICATIONS

This application claims the benefit of Chinese Patent Application No. 200910128671.5 filed Mar. 16, 2009, which is hereby incorporated by reference in its entirety.

BACKGROUND OF THE INVENTION

Embodiments described herein relate to a panel support device and an X-ray apparatus, and more particularly, to a panel support device that detachably supports an X-ray receiving panel and an X-ray apparatus including the panel support device.

An X-ray apparatus irradiates an X-ray from an X-ray irradiator onto an object, and receives the transmitted X-ray by an X-ray receiver, thereby forming a fluoroscopic image. As one type of an X-ray apparatus, there is an X-ray apparatus using a flat panel type X-ray sensor. The flat panel type X-ray sensor receives an X-ray by a two-dimensional array that includes a plurality of X-ray receiving elements (for example, see Japanese Unexamined Patent Publication No. 11 (1999)-155850 (paragraph Nos. [0012] to [0014] and [0021], FIGS. 2 to 4)).

The flat panel type X-ray sensor is detachably supported, if necessary. For example, the structure where a mounting piece of the flat panel type X-ray sensor is inserted into an inner case having the configuration of a double rectangular case and is fixed by bolts has been employed as a support mechanism (for example, see Japanese Unexamined Patent Publication No. 11 (1999)-188022 (paragraph Nos. [0012] and [0018], FIGS. 1, 2, and 3)).

BRIEF DESCRIPTION OF THE INVENTION

As for the above-mentioned support mechanism, a plurality of processes, such as a process for inserting or separating the mounting piece into or from the inner case and a process for tightening or loosening the bolts, are required to attach and detach the flat panel type X-ray sensor, which is troublesome.

Embodiments of the invention provide a panel support device which an X-ray receiving panel may be attached and detached by a simple operation, and an X-ray apparatus including the panel support device.

In a first aspect of the invention, a panel support device detachably supports an X-ray receiving panel. The panel support device includes a support plate configured to be in contact with the surface of the panel opposite to an X-ray receiving surface of the panel while the panel is mounted, a locking member for locking the panel on the support plate while the panel is mounted, and a drive device for driving the locking member so that the locking member is withdrawn from a locking position when the panel approaches the support plate and the locking member returns to the locking position when the panel comes in contact with the support plate during a process for mounting the panel.

In a second aspect of the invention, in the panel support device according to the first aspect, the locking member may be urged by a spring in the return direction.

In a third aspect of the invention, in the panel support device according to the first aspect, the support plate may include receiving members that support one side of the panel while the panel is mounted, and the locking member may lock the other side of the panel facing the one side of the panel while the panel is mounted.

In a fourth aspect of the invention, in the panel support device according to the first aspect, the locking member may include rotating shafts that are provided parallel to an edge of the support plate, and the drive device may rotate the rotating shafts in normal and reverse directions so that the locking member is withdrawn and returns.

In a fifth aspect of the invention, in the panel support device according to the fourth aspect, the drive device may include a lever of which one end is pushed by the panel approaching the support plate in the process for mounting the panel and rotated.

In a sixth aspect of the invention, in the panel support device according to the fifth aspect, the lever may be urged by a spring in a direction opposite to the rotation direction of the lever when one end of the lever is urged by the panel.

In a seventh aspect of the invention, in the panel support device according to the sixth aspect, the lever may rotate the rotating shafts of the locking member in the withdrawal direction by the rotation of the other end of the lever when one end of the lever is pushed by the panel.

In an eighth second aspect of the invention, in the panel support device according to the seventh aspect, the rotating shaft of the locking member may include a cam driven at the other end of the lever.

In a ninth aspect of the invention, in the panel support device according to the eighth aspect, the cam may be rotated about an eccentric shaft, which is parallel to the rotating shafts of the locking member, only in a direction opposite to the withdrawal direction of the rotating shaft.

In a tenth aspect of the invention, in the panel support device according to the ninth aspect, the cam may include a claw at a portion thereof, which is driven by the other end of the lever.

In an eleventh aspect of the invention, an X-ray apparatus includes an X-ray irradiation device and a panel support device that detachably supports an X-ray receiving panel. The panel support device includes a support plate configured to be in contact with the surface of the panel opposite to an X-ray receiving surface of the panel while the panel is mounted, a locking member for locking the panel on the support plate while the panel is mounted, and a drive device for driving the locking member so that the locking member is withdrawn from a locking position when the panel approaches the support plate and the locking member returns to the locking position when the panel comes in contact with the support plate during the process for mounting the panel.

In a twelfth aspect of the invention, in the X-ray apparatus according to the eleventh aspect, the locking member may be urged by a spring in the return direction.

In a thirteenth aspect of the invention, in the X-ray apparatus according to the eleventh aspect, the support plate may include receiving members that support one side of the panel while the panel is mounted, and the locking member may lock the other side of the panel facing the one side of the panel while the panel is mounted.

In a fourteenth aspect of the invention, in the X-ray apparatus according to the eleventh aspect, the locking member may include rotating shafts that are provided parallel to an edge of the support plate, and the drive device may rotate the rotating shafts in normal and reverse directions so that the locking member is withdrawn and returns.

In a fifteenth aspect of the invention, in the X-ray apparatus according to the fourteenth aspect, the drive device may include a lever of which one end is pushed by the panel approaching the support plate during the process for mounting the panel and rotated.

In a sixteenth aspect of the invention, in the X-ray apparatus according to the fifteenth aspect, the lever may be urged by a spring in a direction opposite to the rotation direction of the lever when one end of the lever is pushed by the panel.

In a seventeenth aspect of the invention, in the X-ray apparatus according to the sixteenth aspect, the lever may rotate the rotating shafts of the locking member in the withdrawal direction by the rotation of the other end of the lever when one end of the lever is pushed by the panel.

In an eighteenth second aspect of the invention, in the X-ray apparatus according to the seventeenth aspect, the rotating shaft of the locking member may include a cam driven at the other end of the lever.

In a nineteenth aspect of the invention, in the X-ray apparatus according to the eighteenth aspect, the cam may be rotated about an eccentric shaft, which is parallel to the rotating shafts of the locking member, only in a direction opposite to the withdrawal direction of the rotating shaft.

In a twentieth aspect of the invention, in the X-ray apparatus according to the nineteenth aspect, the cam may include a claw at a portion thereof, which is driven by the other end of the lever.

In to the first aspect of invention, a panel support device detachably supports an X-ray receiving panel. The panel support device includes a support plate configured to be in contact with the surface of the panel opposite to an X-ray receiving surface of the panel while the panel is mounted, a locking member for locking the panel on the support plate while the panel is mounted, and a drive device for driving the locking member so that the locking member is withdrawn from a locking position when the panel approaches the support plate and the locking member returns to the locking position when the panel comes in contact with the support plate during a process for mounting the panel. Therefore, it is possible to embody a panel support device where an X-ray receiving panel may be attached and detached by a simple operation.

According to the eleventh aspect of invention, an X-ray apparatus includes an X-ray irradiation device and a panel support device that detachably supports an X-ray receiving panel. The panel support device includes a support plate configured to be in contact with the surface of the panel opposite to an X-ray receiving surface of the panel while the panel is mounted, a locking member for locking the panel on the support plate while the panel is mounted, and a drive device for driving the locking member so that the locking member is withdrawn from a locking position when the panel approaches the support plate and the locking member returns to the locking position when the panel comes in contact with the support plate in a process for mounting the panel. Therefore, it is possible to embody an X-ray apparatus including a panel support device where an X-ray receiving panel may be attached and detached by a simple operation.

According to the second or twelfth aspect of invention, the locking member is urged by a spring in the return direction. Therefore, the locking member can return to the locking position by itself.

According to the third or thirteenth aspect of invention, the support plate includes receiving members that support one side of the panel while the panel is mounted, and the locking member locks the other side of the panel facing the one side of the panel while the panel is mounted. Therefore, the locking member can be rotated relative to the support plate.

According to the fourth or fourteenth aspect of invention, the locking member includes rotating shafts that are provided parallel to an edge of the support plate, and the drive device rotates the rotating shafts in normal and reverse directions so that the locking member is withdrawn and returns. Therefore, the support member can be easily withdrawn and return.

According to the fifth or fifteenth aspect of invention, the drive device includes a lever of which one end is pushed by the panel approaching the support plate during the process for mounting the panel and rotated. Therefore, the drive device can be operated while being interlocked with the panel approaching the support plate.

According to the sixth or sixteenth aspect of invention, the lever is urged by a spring in a direction opposite to the rotation direction of the lever when one end of the lever is pushed by the panel. Therefore, the lever can return to an initial position by itself.

According to the seventh or seventeenth aspect of invention, the lever rotates the rotating shafts of the locking member in the withdrawal direction by the rotation of the other end of the lever when one end of the lever is pushed by the panel. Therefore, the rotating shafts of the locking member can be rotated when the panel approaches the support plate.

According to the eighth or eighteenth aspect of invention, the rotating shaft of the locking member includes a cam driven at the other end of the lever. Therefore, it is possible to improve the driveability of the rotating shaft of the locking member that is driven by the lever.

According to the ninth or nineteenth aspect of invention, the cam may be rotated about an eccentric shaft, which is parallel to the rotating shafts of the locking member, only in a direction opposite to the withdrawal direction of the rotating shaft. Therefore, the rotation of the lever, which returns to an initial position, is not prevented.

According to the tenth or twentieth aspect of invention, the cam includes a claw at a portion thereof, which is driven by the other end of the lever. Therefore, it is possible to improve the driveability of the cam that is driven by the lever.

BRIEF DESCRIPTION OF THE DRAWINGS

FIGS. 6A and 6B are views showing a portion that includes a locking part and the drive mechanism.

DETAILED DESCRIPTION OF THE INVENTION

Embodiments of the invention will be described in detail below with reference to drawings. Meanwhile, the invention is not limited to the embodiments described herein.

Figure 1:
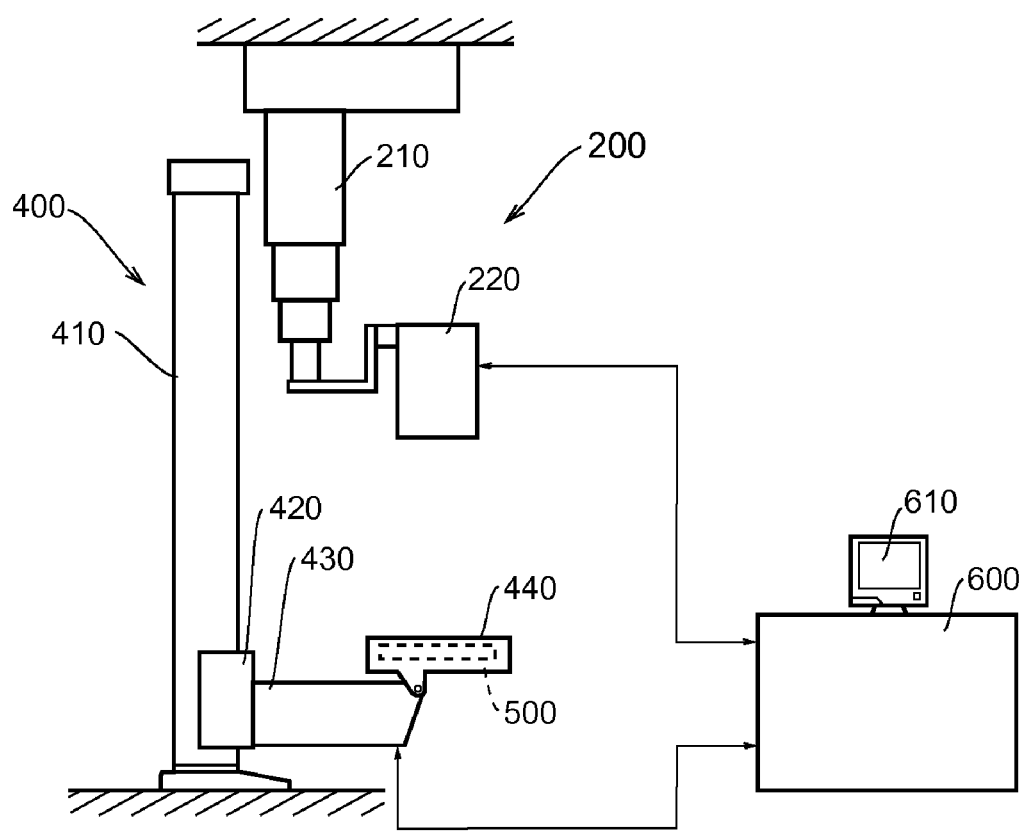
FIG. 1 is a view showing the configuration of an X-ray apparatus according to an example of a preferred embodiment of the invention.

FIG. 1 schematically shows the configuration of an X-ray apparatus. The apparatus is an example of a preferred embodiment of the invention. The configuration of the apparatus shows an example of the X-ray apparatus according to the preferred embodiment of the invention.

As shown in FIG. 1, the apparatus includes an X-ray irradiation device 200 and an X-ray detection device 400. In the X-ray irradiation device 200, an X-ray irradiator 220 is mounted at the end of a column 210 that extends downward from the ceiling. The X-ray irradiator 220 may change an X-ray irradiation direction. The column 210, which supports the X-ray irradiator 220, can be expanded and contracted in a longitudinal direction, and can be moved along the ceiling in a horizontal direction. The X-ray irradiation device 200 is an example of an X-ray irradiation device of the invention.

In the X-ray detection device 400, a carriage 420 is mounted on a column 410 perpendicular to a floor so as to be moved upward and downward, an arm 430 is horizontally mounted to the carriage 420, and a detector housing 440 is mounted at the end of the arm 430. Accordingly, the X-ray detection device 400 is a so-called wall stand type X-ray detection device.

The detector housing 440 is a flat rectangular parallelepiped structure, and receives an X-ray receiving panel 500 therein. The detector housing 440 can be tilted so that an X-ray incident surface corresponds to a vertical, horizontal, or arbitrary angle according to an X-ray incident direction.

For example, the panel 500 is a flat panel type X-ray sensor that receives an X-ray by a two-dimensional array composed of a plurality of X-ray receiving elements. Meanwhile, the panel 500 is not limited to the flat panel type X-ray sensor, and may be a film cassette that receives an X-ray film. The panel 500 is an example of an X-ray receiving panel of the invention.

If the panel 500 is a flat panel type X-ray sensor, an X-ray detection signal is input to an operator console 600 from the detector housing 440. The operator console 600 reconstructs a fluoroscopic image of an imaging object on the basis of an input signal input from the detector housing 440, and displays the fluoroscopic image on a display 610. If the panel 500 is a film cassette, a fluoroscopic image is visualized by developing an X-ray film.

The operator console 600 controls the X-ray irradiation device 200 and the X-ray detection device 400. As for the X-ray irradiation device 200, the positions of the X-ray irradiator 220 in the horizontal and vertical directions, the X-ray irradiation direction, X-ray intensity, and irradiation timing are controlled.

As for the X-ray detection device 400, the height of the detector housing 440 is controlled in accordance with the X-ray irradiator 220, and the angle of the detector housing 440 is adjusted, so that the direction of the X-ray incident surface is controlled in accordance with the X-ray incident direction.

Figure 2:
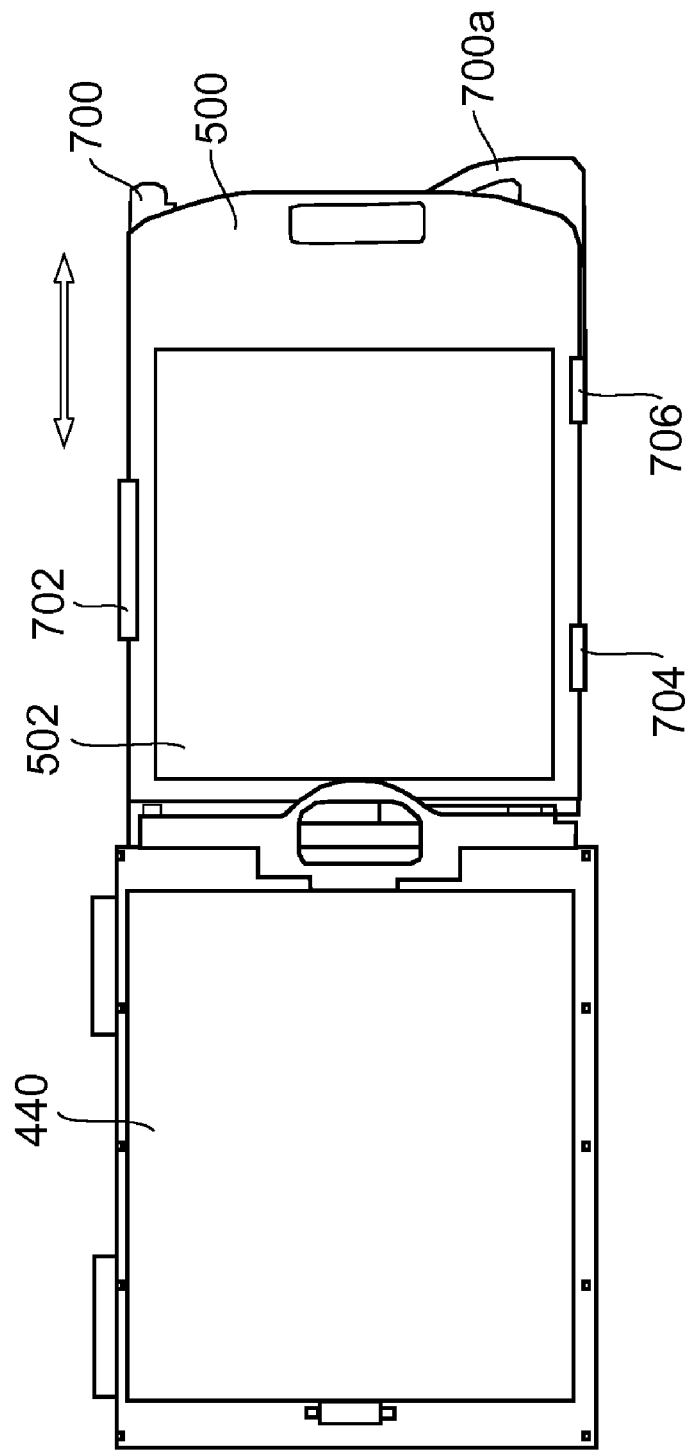
FIG. 2 is a view showing that a panel is drawn from a detector housing.

FIG. 2 shows that the panel 500 is drawn from the detector housing 440. As shown in FIG. 2, the panel 500 is supported by a support plate 700. The support plate 700 is provided with a handle 700a, and can be taken in and out of the detector housing 440 like a drawer.

While the rear surface of the panel 500, that is, the surface of the panel opposite to an X-ray incident surface 502 comes in contact with the front surface of the support plate 700, one side (an upper side in the drawing) of two sides of the panel, which face each other and are parallel to a direction where the support plate 700 is taken in and out, is locked by a locking part 702 and the other side (a lower side in the drawing) is supported by receiving parts 704 and 706. The panel 500, which is locked by the locking part 702, can be released. Accordingly, the panel 500 can be attached and detached to and from the support plate 700.

Figure 3:
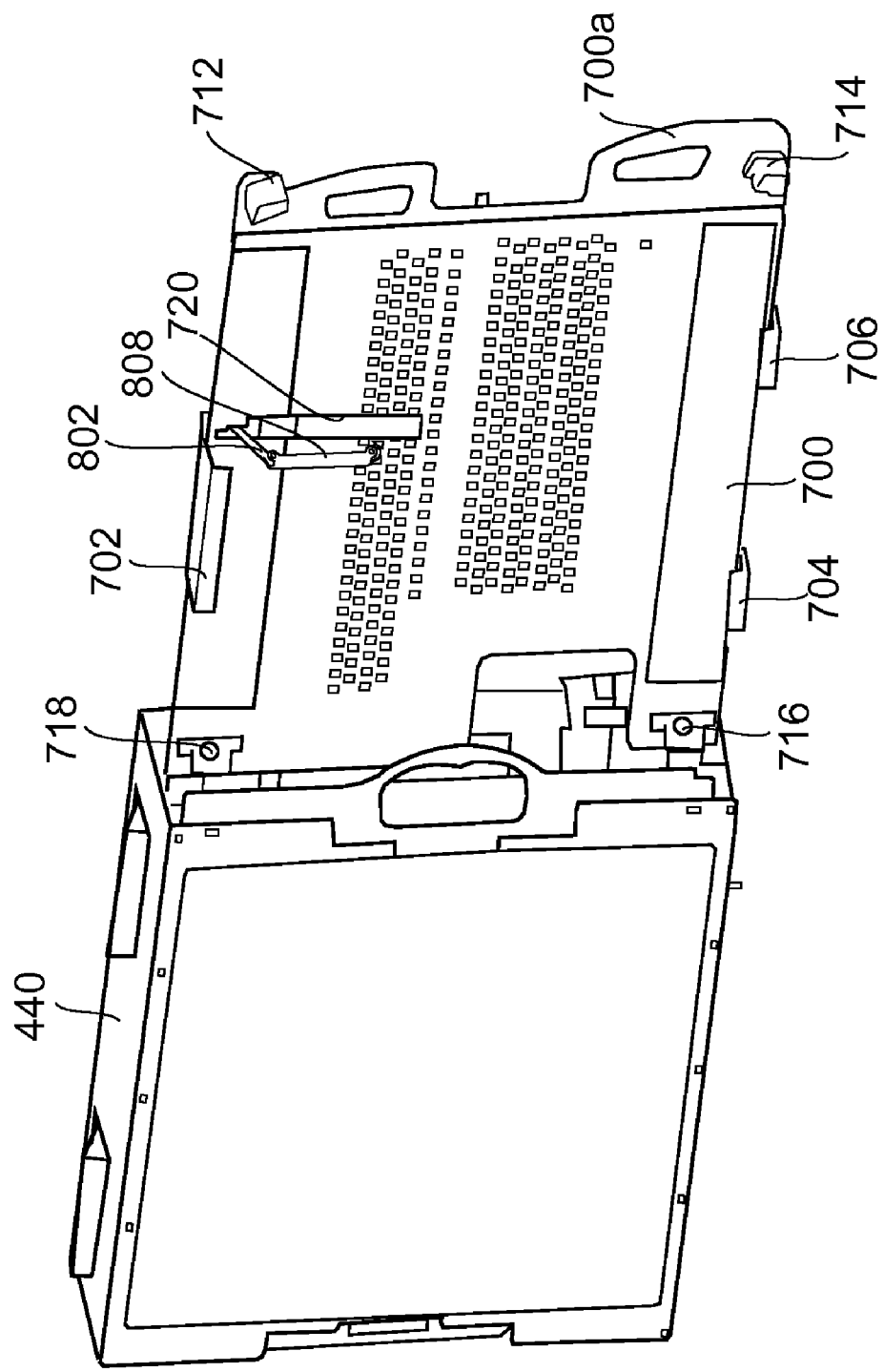
FIG. 3 is a view showing the configuration of a panel support device according to an example of a preferred embodiment of the invention.

FIG. 3 shows the support plate 700 when the panel 500 is removed. As shown in FIG. 3, the locking part 702 is a plate-like locking part that is bent downward in an L shape, and the receiving parts 704 and 706 are plate-like locking parts that are bent upward in an L shape. All the parts are mounted at the edges of the support plate 700.

When the panel 500 is mounted on the support plate 700, the lower surface of an L-shaped horizontal portion of the locking part 702 comes in contact with the outer peripheral surface of the upper side of the panel 500, the inner surface of a vertical portion thereof comes in contact with the front surface of the upper side of the panel 500, the upper surfaces of L-shaped horizontal portions of the receiving parts 704 and 706 come in contact with the outer peripheral surface of the lower side of the panel 500, and the inner surfaces of vertical portions thereof come in contact with the front surface of the lower side of the panel 500.

Protrusions 712, 714, 716, and 718 for positioning the panel 500 are formed in the vicinity of four corners on the front surface of the support plate 700. The panel 500 is supported while coming in contact with the inner portions of the protrusions 712, 714, 716, and 718, the locking part 702, and the receiving parts 704 and 706.

A slit 720 is formed in the support plate 700, and a lever 802 protrudes forward and downward through the slit 720. The lever 802 includes a pivot, which is supported by a bearing provided on the rear surface of the support plate 700, at the rear end thereof. Accordingly, the lever 802 can be rotated about the pivot in a direction perpendicular to the surface of the support plate 700. A reaction force generated by a spring is applied to a rotation of the lever 802.

A vertical bar 808 extends downward from the end of the lever 802. The connection portion between the vertical bar 808 and the lever 802 is formed of a hinge to which a reaction force is applied by a spring. The spring is neutral in a state shown in the drawing.

Figure 4:
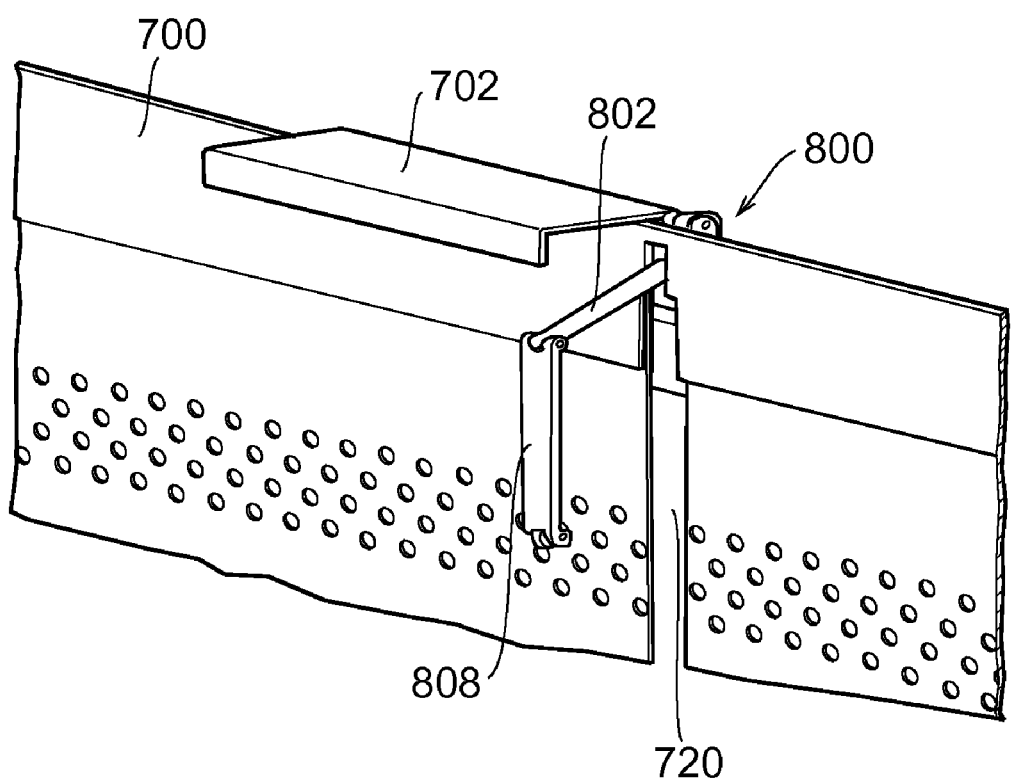
FIG. 4 is an enlarged view showing the configuration in the vicinity of a locking part.

FIG. 4 is an enlarged view showing the configuration in the vicinity of the locking part 702. As shown in FIG. 4, the support plate 700 includes a drive mechanism 800 for the locking part 702 on the rear surface thereof. The lever 802 and the vertical bar 808 are a part of the drive mechanism 800.

Figure 5:
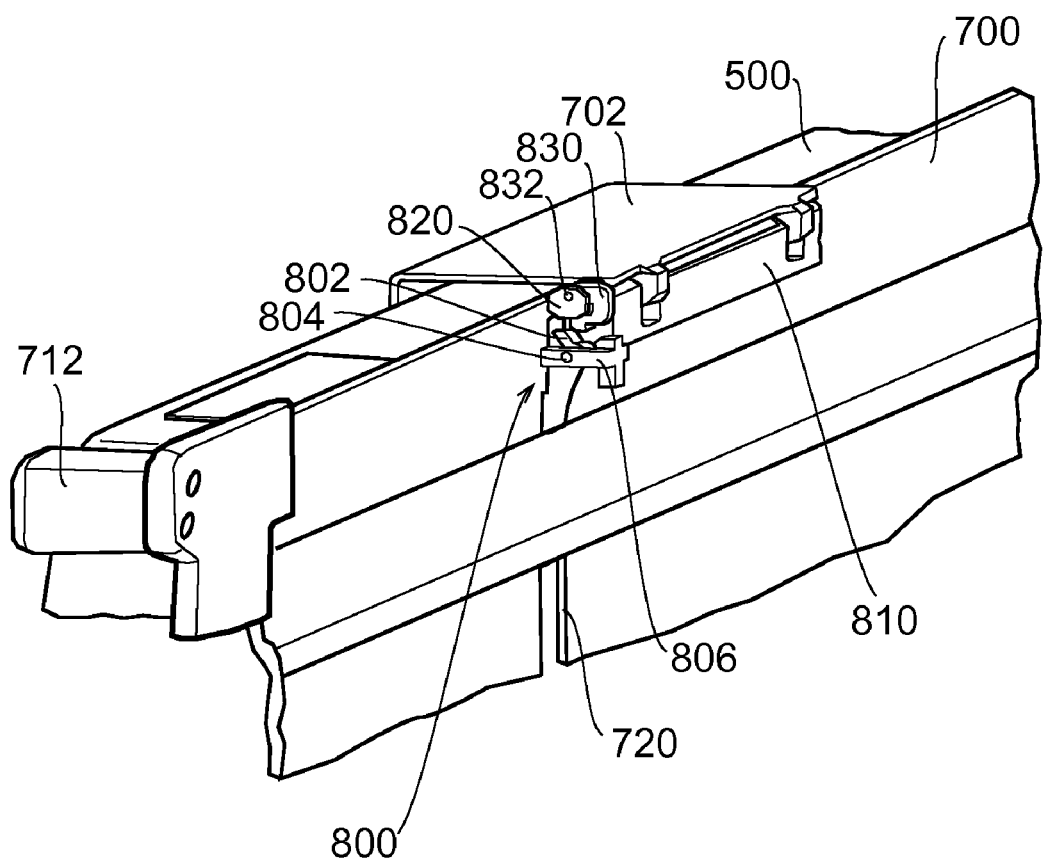
FIG. 5 is a view showing the configuration of a drive mechanism on the rear surface of a support plate.

FIG. 5 shows the configuration of the drive mechanism 800 that is provided on the rear surface of the support plate 700. FIG. 5 shows that the panel 500 is supported by the support plate 700 and the panel 500 is locked by the locking part 702. The rear surface of the panel 500 comes in contact with the front surface of the support plate 700, and the lower surface of the horizontal portion of the locking part 702 and the inner surface of the vertical portion thereof come in contact with the outer peripheral surface and the front surface of the upper side of the panel 500, respectively.

The support plate 700, the locking part 702, and the drive mechanism 800 form a panel support device. The panel support device is an example of a preferred embodiment of the invention. The configuration of the panel support device shows an example of the panel support device according to the preferred embodiment of the invention.

The support plate 700 is an example of a support plate in the invention. The locking part 702 is an example of a locking member of the invention. The receiving parts 704 and 706 are examples of receiving members of the invention. The drive mechanism 800 is an example of a drive device of the invention. The lever 802 is an example of a lever of the invention.

The drive mechanism 800 includes a bracket 810. The bracket 810 is a plate-like member having a predetermined thickness, and is fixed to the upper portion of the rear surface of the support plate 700 at a position deviated from the slit 720 in a horizontal direction.

The upper portion of the bracket 810 is formed of bearings for a rotating shaft 820. The rear end of the locking part 702 is fixed to the rotating shaft 820. Accordingly, the locking part 702 can be rotated together with the rotating shaft 820. A reaction force generated by a spring is applied to a rotation of the locking part 702. The spring is neutral in a state shown in the drawing. The rotating shaft 820 is an example of a rotating shaft of the invention.

The rotating shaft 820 extends to the upper portion of the slit 720. A cam 830 is mounted to the extension portion thereof by an eccentric pin 832. The cam 830 is positioned above the slit 720. The eccentric pin 832 is eccentric with respect to the axis of the rotating shaft 820.

A bearing 806 is provided in the vicinity of an upper end of the slit 720 below the cam 830. The pivot 804 of the lever 802 is rotatably supported by the bearing 806. The rear end of the lever 802 extends beyond the pivot 804.

FIGS. 6A and 6B show a portion that includes the locking part 702 and the drive mechanism 800. FIGS. 6A and 6B are views seen from the rear and front sides, respectively. The vertical bar 808 includes a roller 808a at the lower end thereof. The lever 802 is in a state where the lever is rotated by a reaction force of the leaf spring 804a to the maximum extent. The leaf spring 804a is an example of a spring of the invention.

As shown in FIGS. 6A and 6B, the bracket 810 supports rotating shafts 820 and 820' by bearings that are provided on left and right sides, respectively. The rear end of the locking part 702 is fixed to the rotating shafts 820 and 820'. The rotating shafts 820 and 820' are provided with coil springs 822 and 822', which generate reaction forces, respectively. Each of the coil springs 822 and 822' is an example of a spring of the invention.

Figure 7:
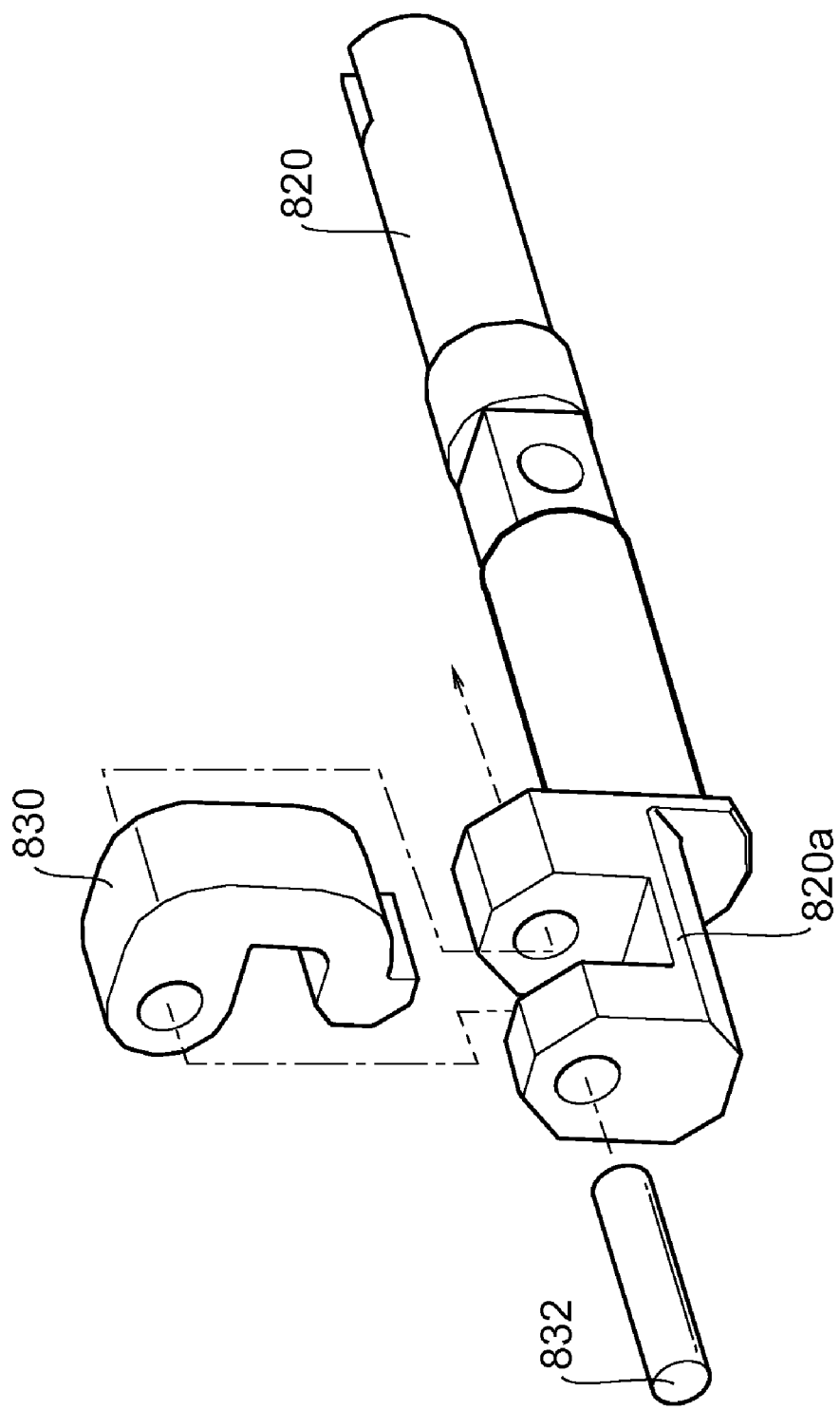
FIG. 7 is an exploded view showing the configuration of a portion that includes a rotating shaft, a cam, and an eccentric pin.

FIG. 7 is an exploded view showing the configuration of a portion that includes the rotating shaft 820, the cam 830, and the eccentric pin 832. As shown in FIG. 7, the extension portion of the rotating shaft 820 is formed of a U-shaped cam mounting portion 820a. A C-shaped cam 830 is combined with the cam mounting portion 820a so as to loosen in a horizontal direction, and is connected by the eccentric pin 832 that passes through a portion near the U-shaped end. Accordingly, the cam 830 cannot be rotated about the eccentric pin 832 in a clockwise direction, and can be rotated about the eccentric pin 832 only in a counterclockwise direction. A reaction force generated by the spring may be applied to the cam 830 that is rotated in a counterclockwise direction.

Figure 8:
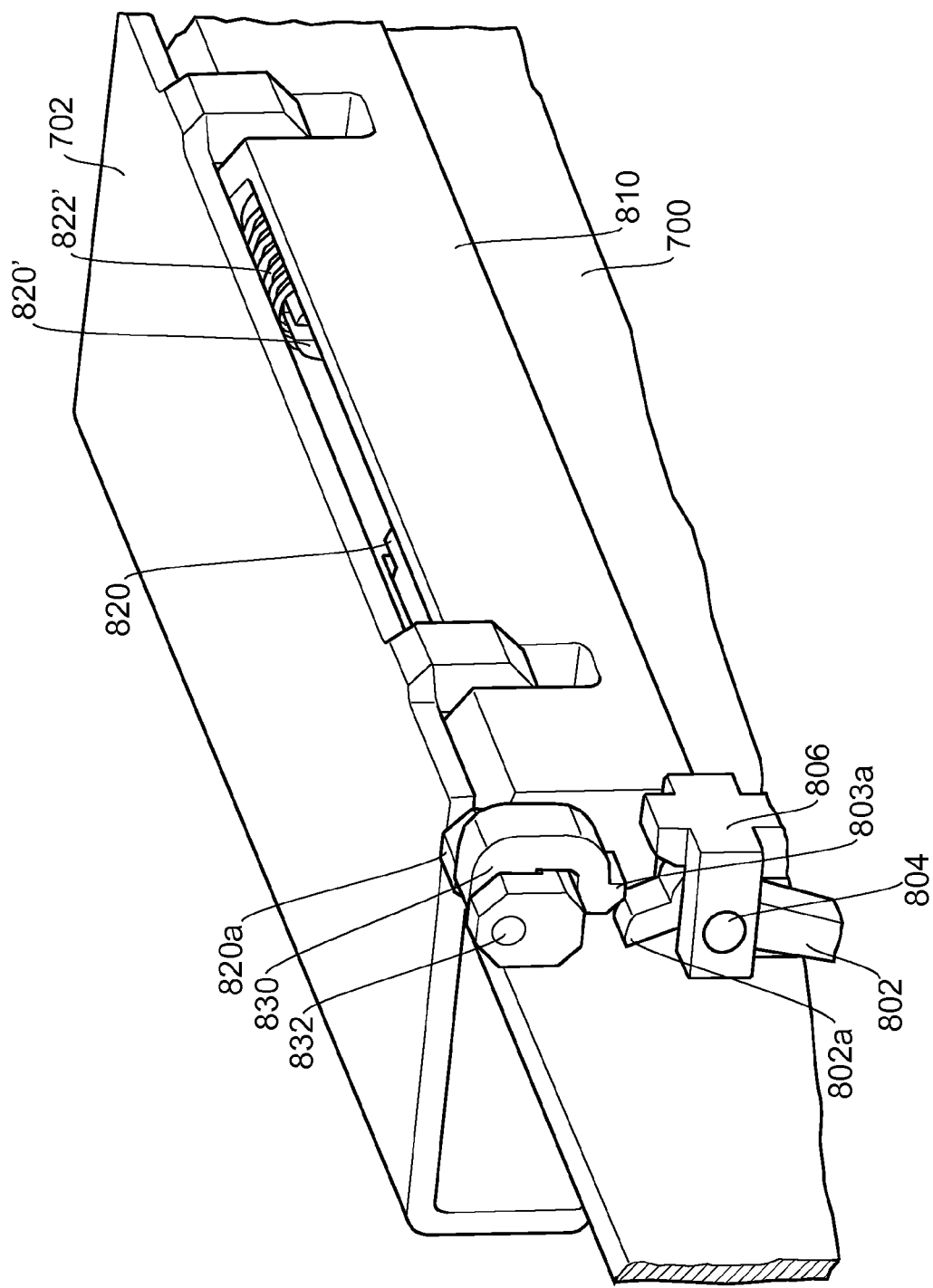
FIG. 8 is a detailed view showing a relationship between the cam and a lever.

FIG. 8 shows a relationship between the cam 830 and the lever 802 in detail. As shown in FIG. 8, a claw 830a is formed at the lower portion of the cam 830. A claw 802a is formed at the rear end of the lever 802. The claw 802a corresponds to the claw 830a. The cam 830 is an example of a cam of the invention. The claw 830a is an example of a claw of the invention.

The sum of the distance between the axis of the rotating shaft 820 and the end of the claw 830a and the distance between an axis of the pivot 804 and the end of the claw 802a is larger than the distance between the axis of the rotating shaft 820 and the axis of the pivot 804. Accordingly, the claw 802a and the claw 830a may be engaged with each other.

Therefore, when the lever 802 is rotated in the clockwise direction from the state shown in the drawing, the claw 802a of the lever 802 comes in contact with the claw 830a of the cam 830 from the left side and then pushes the cam 830 toward the right side. The pushed cam 830 is rotated about the eccentric pin 832 in the counterclockwise direction. However, when the end of the claw 802a is separated from the end of the claw 830a due to further rotation of the lever 802, the pushed cam is rotated in the clockwise direction due to its own weight and thus returns to its original position. During this period, the rotating shaft 820 is not rotated and is maintained in the state shown in the drawing. Therefore, the locking part 702 is also maintained at a locking position.

When the lever 802 is rotated in the clockwise direction to the maximum extent, the claw 802a is moved to the right side of the claw 830a due to the above-mentioned movement of the cam 830. If the lever 802 is rotated in the counterclockwise direction from this state, the claw 802a comes in contact with the claw 830a from the right side and pushes the cam 830 toward the left side.

Since the pushed cam 830 cannot be rotated about the eccentric pin 832 in the clockwise direction, the pushed cam is rotated in the clockwise direction together with the rotating shaft 820. The locking part 702 is also rotated in the clockwise direction together with the rotating shaft 820, so that the locking part 702 is withdrawn from the locking position.

The reaction forces of the coil springs 822 and 822' are applied to the locking part 702 that is rotated in the clockwise direction. Accordingly, when the end of the claw 802a is separated from the end of the claw 830a due to further rotation of the lever 802, the locking part 702 is rotated in the counterclockwise direction by the reaction forces of the coil springs 822 and 822' and thus returns to the locking position.

The above-mentioned movement of the locking part 702 is interlocked with the mounting of the panel 500 on the support plate 700. The movement of the locking part 702 will be described below with reference to FIGS. 9 to 13 that show a process for mounting the panel 500.

Figure 9:
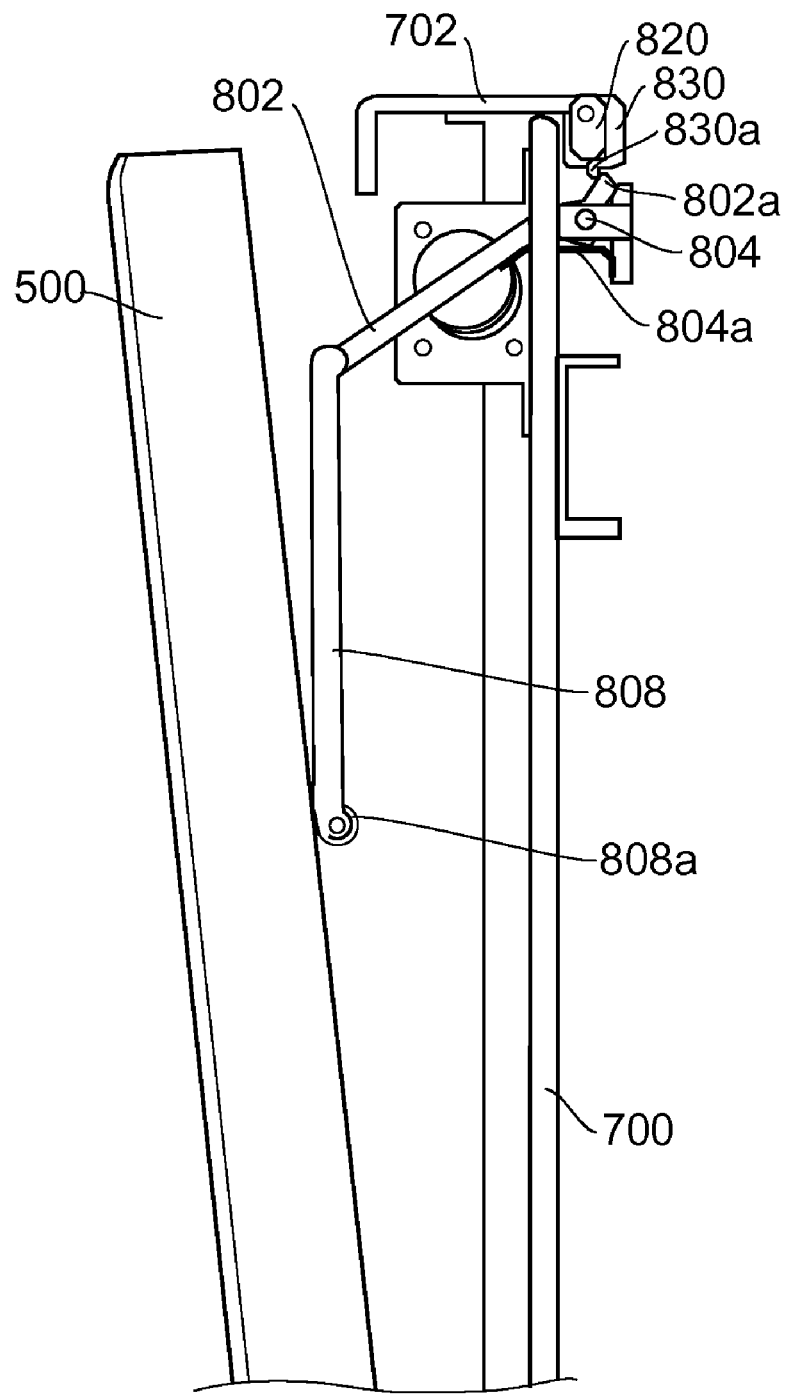
FIG. 9 is a view illustrating a process for mounting the panel on the support plate.

First, the lower side of the panel 500 is inserted into the receiving parts 704 and 706 of the support plate 700. Accordingly, as shown in FIG. 9, the panel 500 is tilted with respected to the support plate 700, and the rear surface thereof comes in contact with the roller 808a that is provided at the lower end of the vertical bar 808.

In this case, the lever 802 is in a state where the lever is rotated in the clockwise direction by a reaction force of the leaf spring 804a to the maximum extent. The locking part 702 is in the locking position, and the claw 830a of the cam 830 is oriented downward. Accordingly, the claw 802a of the lever 802 is positioned on the right side of the claw 830a of the cam 830.

Figure 10:
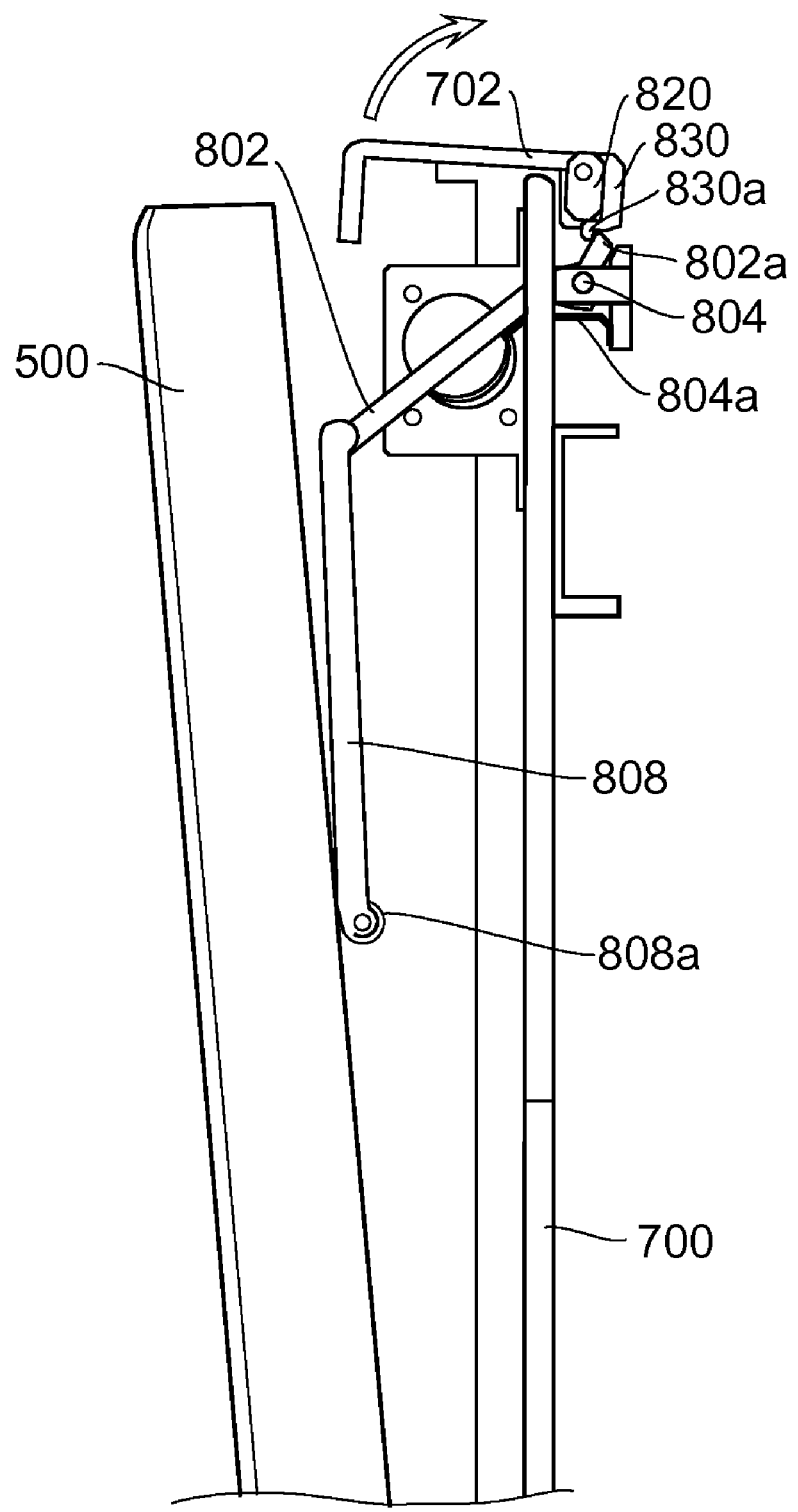
FIG. 10 is a view illustrating a process for mounting the panel on the support plate.

If the panel 500 is pressed against the support plate 700 from this state and the upper side approaches the locking part 702, the vertical bar 808 is pushed toward the right side as shown in FIG. 10. Accordingly, the lever 802, which is connected by a hinge having a spring, is rotated about the pivot 804 in the counterclockwise direction.

Since the lever 802 is rotated in the counterclockwise direction, the cam 830 of which the claw 830a is pushed by the claw 802a of the lever 802 is rotated in the clockwise direction together with the rotating shaft 820. Accordingly, the locking part 702 is rotated in the clockwise direction, so that the locking position begins to be withdrawn from the locking position.

Figure 11:
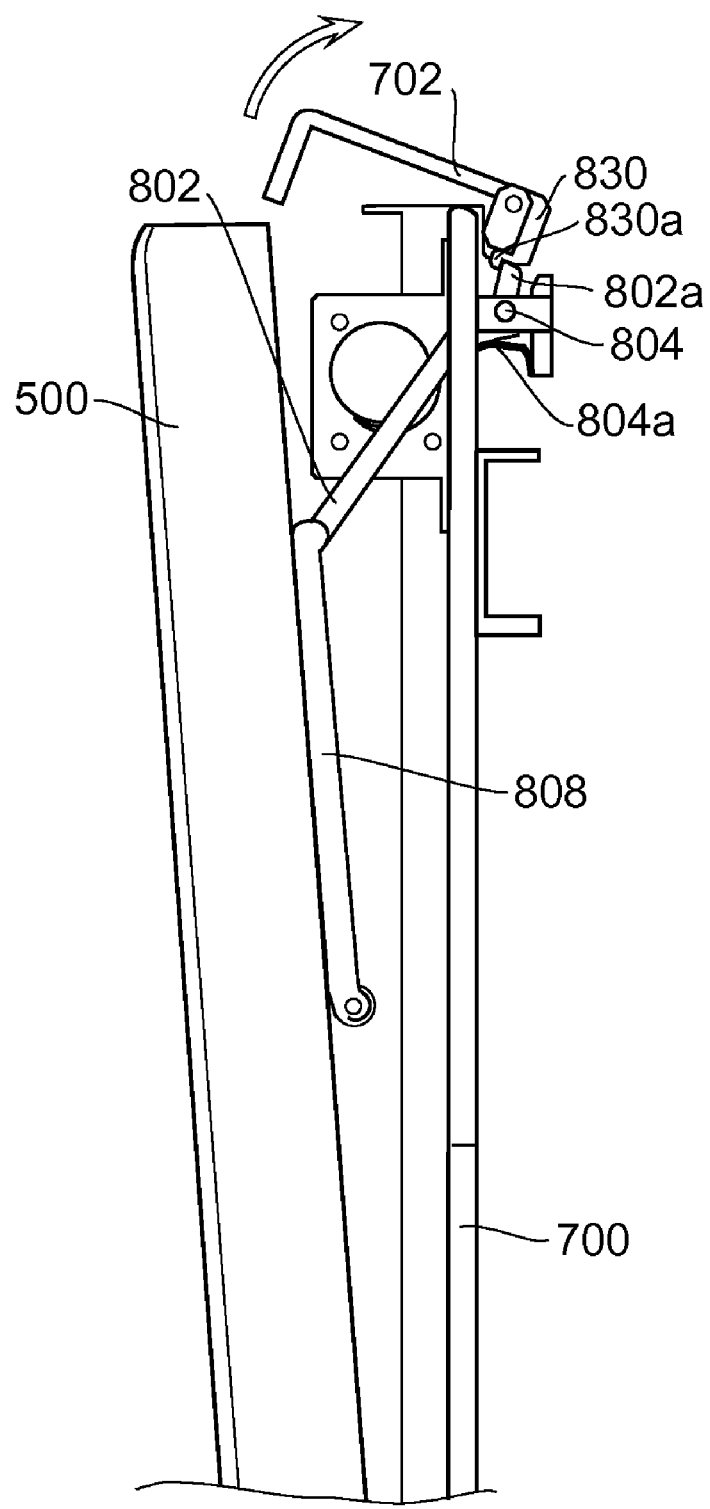
FIG. 11 is a view illustrating a process for mounting the panel on the support plate.

As the panel 500 is pressed, the rotation angle of the locking part 702, that is, the withdrawal amount is increased as shown in FIG. 11. Therefore, the locking part 702 does not prevent the upper side of the panel 500 from approaching the support plate 700.

Figure 12:
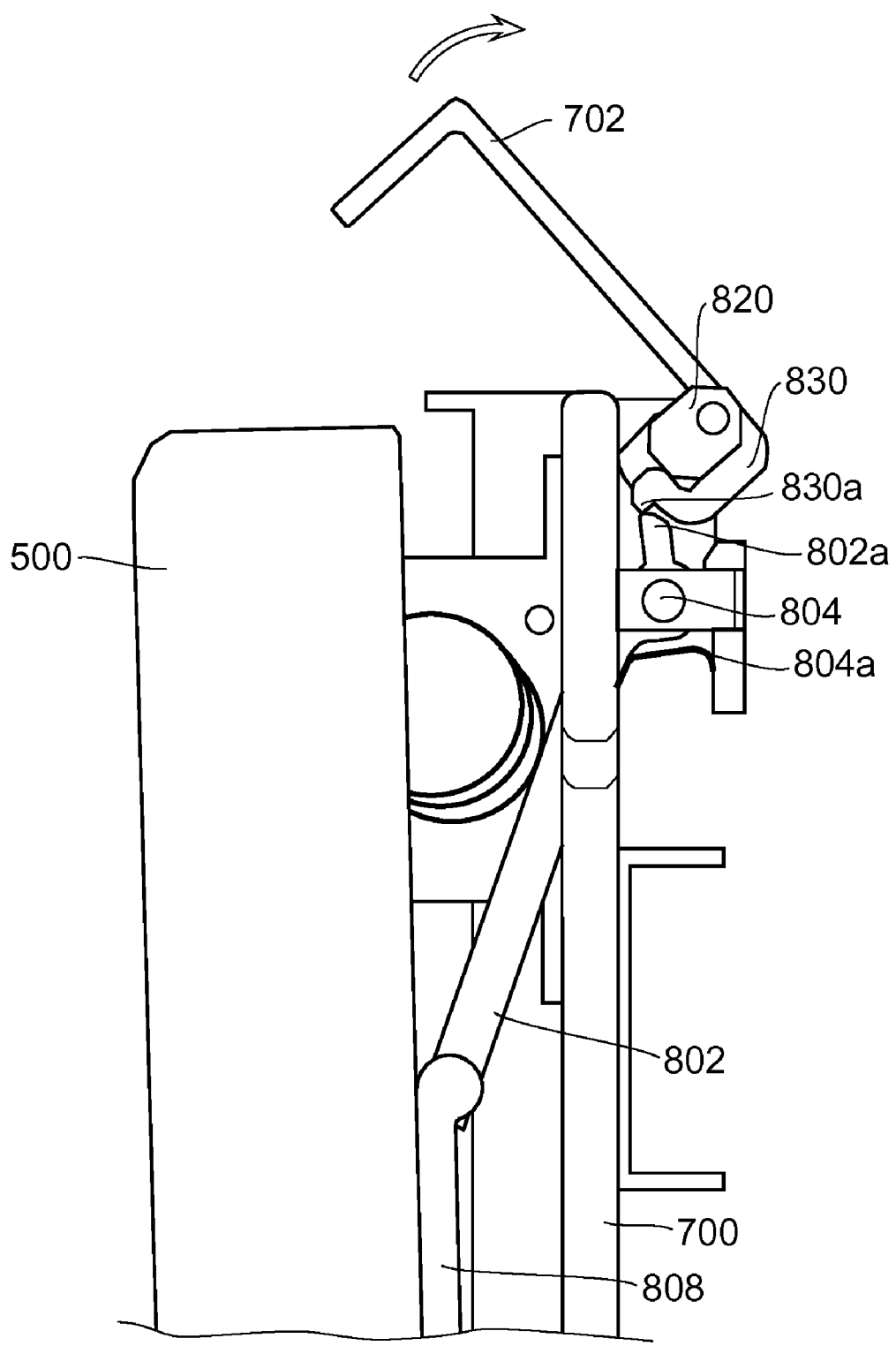
FIG. 12 is a view illustrating a process for mounting the panel on the support plate.
Figure 13:
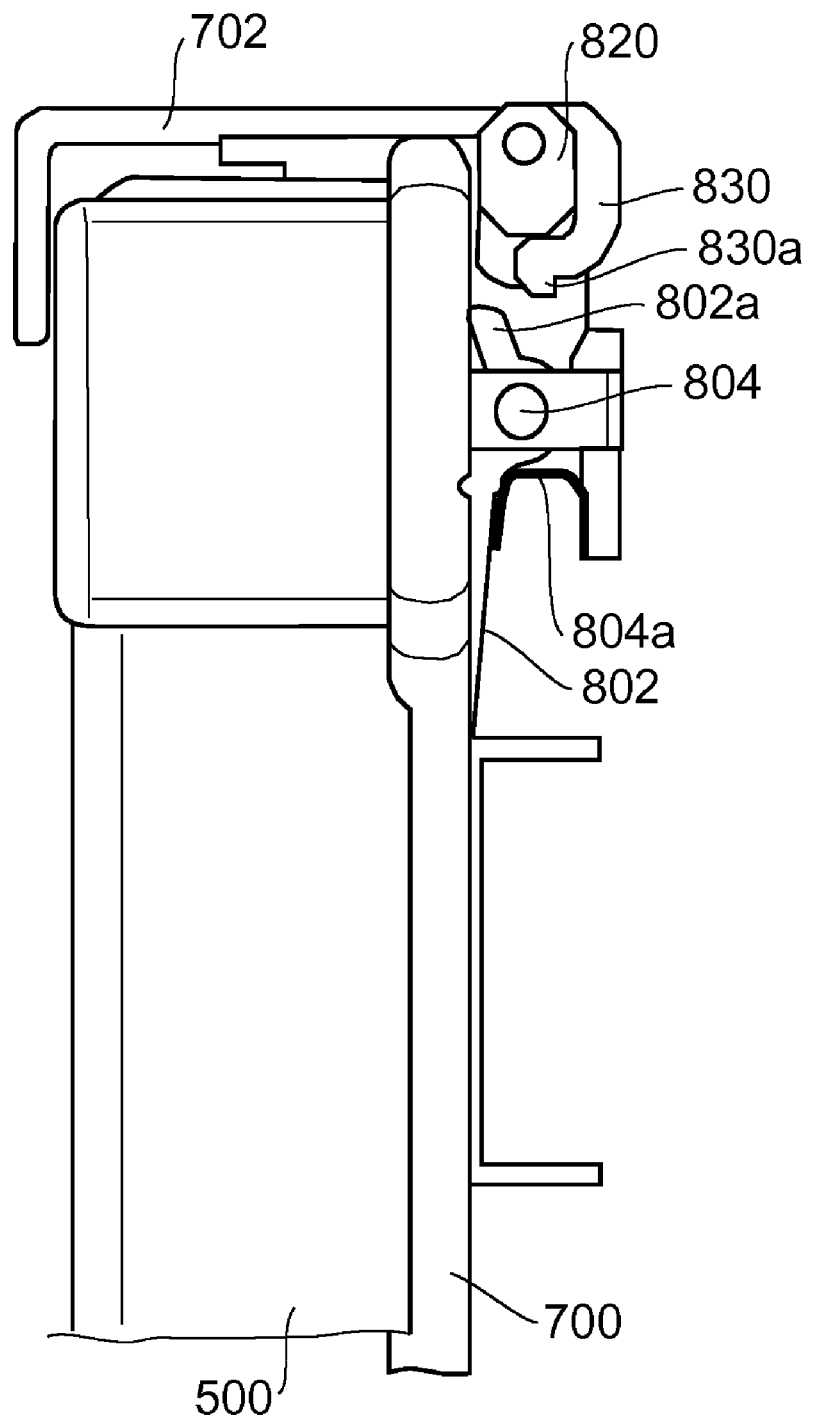
FIG. 13 is a view illustrating a process for mounting the panel on the support plate.

As the upper side of the panel 500 further approaches the support plate, the claw 802a of the lever 802 and the claw 830a of the cam 830 narrowly come in contact with each other as shown in FIG. 12. If the panel 500 further approaches the support plate from this state, the lever 802 is further rotated in the clockwise direction, so that the claw 802a is separated from the claw 830a. At this time, the locking part 702 returns to the locking position due to the forces of the coil springs 822 and 822', and the upper side of the panel 500 is locked on the support plate 700 as shown in FIG. 13.

In this way, the locking part 702 is withdrawn from the locking position once when the panel 500 approaches the support plate 700, and returns to the locking position when the panel 500 comes in contact with the support plate 700. Accordingly, the mounting of the panel can be performed by a simple operation that presses the upper side of the panel against the support plate 700 after the lower side thereof is inserted into the receiving parts 704 and 706.

In order to remove the panel 500 from the support plate 700, the locked panel 500 may be released by turning upward the vertical portion of the locking part 702 with a thumb. Accordingly, the panel 500 is pushed by the lever 802 that is urged by the leaf spring 804a, thereby being separated from the support plate 700. Therefore, it is possible to also remove the panel 500 by a simple operation.

What is claimed is:

1. A panel support device configured to detachably support an X-ray receiving panel, the panel support device comprising:
    a support plate configured to be in contact with a first surface of the panel opposite to an X-ray receiving surface of the panel while the panel is mounted;
    a locking member comprising at least one rotating shaft that is provided parallel to an edge of the support plate, the locking member configured to lock the panel on the support plate while the panel is mounted; and
    a drive device configured to drive the locking member such that the locking member is withdrawn from a locking position when the panel approaches the support plate and the locking member returns to the locking position when the panel comes in contact with the support plate in a process for mounting the panel and configured to rotate the at least one rotating shaft in a normal direction and in a reverse direction such that the locking member is withdrawn and returns.

2. The panel support device according to claim 1, wherein the locking member is urged by a spring in a return direction.

3. The panel support device according to claim 1, wherein:
    the support plate comprises at least one receiving member that supports a first side of the panel while the panel is mounted; and
    the locking member is configured to lock a second side of the panel while the panel is mounted.

4. The panel support device according to claim 1, wherein the drive device comprises a lever comprising a first end that is pushed by the panel approaching the support plate in the process for mounting the panel and is rotated.

5. The panel support device according to claim 4, wherein the lever is pushed by a spring in a direction opposite to the rotation direction of the lever when the first end of the lever is pushed by the panel.

6. The panel support device according to claim 5, wherein the lever is configured to rotate the at least one rotating shaft of the locking member in the withdrawal direction by the rotation of a second end of the lever when the first end of the lever is pushed by the panel.

7. The panel support device according to claim 6, wherein the rotating shaft of the locking member comprises a cam driven at the second end of the lever.

8. The panel support device according to claim 7, wherein the cam is configured to rotate about an eccentric shaft, which is parallel to the at least one rotating shaft of the locking member, only in a direction opposite to the withdrawal direction of the at least one rotating shaft.

9. The panel support device according to claim 8, wherein the cam comprises a claw at a portion thereof, which is driven by the second end of the lever.

10. An X-ray apparatus comprising:
    an X-ray irradiation device; and
    a panel support device configured to detachably support an X-ray receiving panel, the panel support device comprising:
        a support plate configured to be in contact with a first surface of the panel opposite to an X-ray receiving surface of the panel while the panel is mounted;
        a locking member comprising at least one rotating shaft that is provided parallel to an edge of the support plate, the locking member configured to lock the panel on the support plate while the panel is mounted; and
        a drive device configured to drive the locking member such that the locking member is withdrawn from a locking position when the panel approaches the support plate and the locking member returns to the locking position when the panel comes in contact with the support plate in a process for mounting the panel and configured to rotate the at least one rotating shaft in a normal direction and in a reverse direction such that the locking member is withdrawn and returns.

11. The X-ray apparatus according to claim 10, wherein the locking member is urged by a spring in a return direction.

12. The X-ray apparatus according to claim 10, wherein:
    the support plate comprises at least one receiving member that supports a first side of the panel while the panel is mounted; and
    the locking member is configured to lock a second side of the panel while the panel is mounted.

13. The X-ray apparatus according to claim 10, wherein the drive device comprises a lever comprising a first end that is pushed by the panel approaching the support plate in the process for mounting the panel and is rotated.

14. The X-ray apparatus according to claim 13, wherein the lever is pushed by a spring in a direction opposite to the rotation direction of the lever when the first end of the lever is pushed by the panel.

15. The X-ray apparatus according to claim 14, wherein the lever is configured to rotate the at least one rotating shaft of the locking member in the withdrawal direction by the rotation of a second end of the lever when the first end of the lever is pushed by the panel.

16. The X-ray apparatus according to claim 15, wherein the rotating shaft of the locking member comprises a cam driven at the second end of the lever.

17. The X-ray apparatus according to claim 16, wherein the cam is configured to rotate about an eccentric shaft, which is parallel to the at least one rotating shaft of the locking member, only in a direction opposite to the withdrawal direction of the at least one rotating shaft.

18. The X-ray apparatus according to claim 17, wherein the cam comprises a claw at a portion thereof, which is driven by the second end of the lever.

* * * * *